US012704493B2

(12) United States Patent
Adekunle et al.

(10) Patent No.: US 12,704,493 B2
(45) Date of Patent: Aug. 11, 2026

(54) BIOSENSOR FOR WATER TOXICITY MONITORING

(71) Applicant: NATIONAL RESEARCH COUNCIL OF CANADA, Ottawa (CA)

(72) Inventors: Ademola Adekunle, Airdrie (CA); Boris Tartakovsky, Cote St. Luc (CA); André Moreau, Saint-Bruno-de-Montarville (CA); Yehuda Kleiner, Thornhill (CA)

(73) Assignee: NATIONAL RESEARCH COUNCIL OF CANADA, Ottawa (CA)

( * ) Notice: Subject to any disclaimer, the term of this patent is extended or adjusted under 35 U.S.C. 154(b) by 337 days.

(21) Appl. No.: 18/036,785

(22) PCT Filed: Nov. 10, 2021

(86) PCT No.: PCT/CA2021/051597
§ 371 (c)(1),
(2) Date: May 12, 2023

(87) PCT Pub. No.: WO2022/104453
PCT Pub. Date: May 27, 2022

(65) Prior Publication Data

US 2023/0417722 A1 Dec. 28, 2023

Related U.S. Application Data

(60) Provisional application No. 63/115,254, filed on Nov. 18, 2020.

(51) Int. Cl.
*G01N 33/18* (2006.01)
*G01N 27/413* (2006.01)

(52) U.S. Cl.
CPC ....... *G01N 33/1813* (2013.01); *G01N 27/413* (2013.01); *G01N 33/1826* (2013.01)

(58) Field of Classification Search
None
See application file for complete search history.

(56) References Cited

U.S. PATENT DOCUMENTS

| | | | |
|---|---|---|---|
| 8,846,220 | B2 | 9/2014 | Fedorovich |
| 9,551,685 | B2 | 1/2017 | Buck et al. |

(Continued)

FOREIGN PATENT DOCUMENTS

| | | |
|---|---|---|
| CA | 2378580 | 1/2001 |
| CA | 2568166 | 12/2005 |

(Continued)

OTHER PUBLICATIONS

Zhou, S. et al., Microbial fuel cell-based biosensor for toxic carbon monoxide monitoring. Talanta, 2018. 186: p. 368-371.

(Continued)

*Primary Examiner* — Nasima Monsur
(74) *Attorney, Agent, or Firm* — NORTON ROSE FULBRIGHT CANADA LLP

(57) ABSTRACT

There is provided a biosensor for detecting water contaminants. The biosensor has a microbial fuel cell compartment, having (i) at least one opening to allow water into and out of the microbial fuel cell compartment, (ii) an anode comprising electroactive microorganisms, and (iii) a cathode. The anode is electrically and physically separated from the cathode. The anode is anaerobic and comprises electroactive microorganisms. The cathode is aerobic. The biosensor has a storage compartment housing a biodegradable carbon source to supply the biodegradable carbon source to the electroactive microorganisms; an electric impedance load; an electric switch forming an intermittent connection between the microbial fuel cell compartment and the electric impedance load; an electric sensor; and a control system coupled to the electric switch and the electric sensor, receiving a measurement from the electric sensor, and outputting (Continued)

an indication signaling the presence or absence of the water contaminants based on the measurement.

19 Claims, 9 Drawing Sheets

(56) References Cited

U.S. PATENT DOCUMENTS

| | | | | |
|---|---|---|---|---|
| 9,975,119 | B2 | 5/2018 | Sabate Vizcarra et al. | |
| 2007/0218540 | A1* | 9/2007 | Guiot | C02F 3/301 435/262.5 |
| 2007/0259216 | A1* | 11/2007 | Logan | H01M 8/16 429/515 |
| 2009/0142627 | A1* | 6/2009 | Shimomura | H01M 8/16 210/605 |
| 2010/0092804 | A1 | 4/2010 | Borole | |
| 2010/0178530 | A1 | 7/2010 | Min et al. | |
| 2012/0115045 | A1* | 5/2012 | Kapopara | H01M 8/16 429/401 |
| 2013/0011696 | A1 | 1/2013 | Wallin et al. | |
| 2019/0154621 | A1* | 5/2019 | Bitterly | G01N 27/3277 |
| 2019/0225518 | A1 | 7/2019 | Tartakovsky et al. | |

FOREIGN PATENT DOCUMENTS

| | | |
|---|---|---|
| CA | 2787030 | 7/2011 |
| CN | 101882350 | 11/2010 |
| CN | 106290527 | 1/2017 |
| JP | 2007117995 | 5/2007 |
| WO | 2007027730 | 3/2007 |
| WO | 2009104956 | 8/2009 |
| WO | 2018004463 | 1/2018 |

OTHER PUBLICATIONS

Kim, M., et al., A novel biomonitoring system using microbial fuel cells. Journal of Enbironment Monitoring, 2007. 9(12): p. 1323-1328.

Bhatia, R., et al., Combined physico-chemical and biological sensing in environmental monitoring. Biosensors and Bioelectronics, 2003. 18(5): p. 667-674.

Yu, D., et al., Toxicity detection in water containing heavy metal ions with a self-powered microbial fuel cell-based biosensor. Talanta, 2017. 168: p. 210-216.

Stein, N.E., et al Kinetic models for detection of toxicity in a microbial fuel cell based biosensor. Biosensors and Bioelectronics, 2011. 26(7): p. 3115-3120.

Patil, S., F. Hamishc, and U. Schroder, Toxicity response of electroactive microbial biofilms-a decisive feature for potential biosensor and power source applications. ChemPhyChem, 2010. 11(13): p. 2834-2837.

Davila, D., et al Silicon-based microfabricated microbial fuel cell toxicity sensor. Biosensors and Bioelectronics, 2011. 26(5): p. 2426-2430.

Stein, N. E., etal, On-line detection of toxic components using a microbial fuel cell-based biosensor. Journal of Process Control, 2012. 22(9); p. 1755-1761.

Shen, Y., et al., Effect of shear rate on the response of microbial fuel cell toxicity sensor to Cu (II). Bioresource technology, 2013. 136: p. 707-710.

Liu, B., Y. Lei, and B. Li, A batch-mode cube microbial fuel cell based "shock" biosensor for wastewater quality monitoring. Biosensors and Bioelectronics, 2014. 62: p. 308-314.

* cited by examiner

BIOSENSOR FOR WATER TOXICITY MONITORING

CROSS REFERENCE TO RELATED APPLICATION

The present disclosure is a United States National Stage of International Application No. PCT/CA2021/051597, filed on Nov. 10, 2021, which claims priority from U.S. provisional application No. 63/115,254 filed on Nov. 11, 2020, which is incorporated herein by reference in its entirety.

TECHNICAL FIELD

The present disclosure generally relates to the field of biosensors, specifically biosensors that measure the toxicity of water or the presence of water contaminants.

BACKGROUND OF THE ART

Industrial and other human activities release contaminants in water. The types of contaminants can be divided into organic and inorganic toxicants. The presence of these toxic elements or compounds in water results in numerous environmental problems. For example, water containing heavy metals can cause acute and chronic toxicity to humans and marine wildlife. Moreover, toxic chemicals in drinking water reservoirs are an important health concern for human wellbeing. The presence of biodegradable organic compounds in water increases biological and chemical oxygen demand (BOD and COD) concentrations resulting in increased metabolism of microorganisms and decreased oxygen concentration in water.

Conventional toxicity tests are carried out using grab samples transferred for analysis to controlled laboratory environments. This practice is inherently slow in obtaining results and the cost of each test is rather high, rendering continuous monitoring, let alone real-time results, an impossibility. Consequently, short-term toxicity spikes are often missed and major toxicity events are detected after significant delays. Additionally, the accuracy of off-site tests is often compromised because of the differences between site and laboratory conditions.

It is clear that an alarm system capable of detecting a toxicity event quickly and accurately will enable a more rapid response, which may help limit environmental damages and remediation costs. There is therefore a need for a biosensor that is sensitive to a wide range of organic and inorganic toxicants and is capable of continuous and near real-time monitoring.

SUMMARY

In a first aspect there is provided a biosensor for detecting water contaminants comprising: a microbial fuel cell compartment, the microbial fuel cell compartment comprising (i) at least one opening to allow water into and out of the microbial fuel cell compartment, (ii) an anode comprising electroactive microorganisms, and (iii) a cathode, wherein:

- the anode is electrically and physically separated from the cathode,
- the anode is anaerobic and comprises electroactive microorganisms, and
- the cathode is aerobic;
- a storage compartment comprising a biodegradable carbon source, the storage compartment being in communication with the anode to supply the biodegradable carbon source to the electroactive microorganisms;
- an electric impedance load electrically connected to the anode and the cathode thereby forming an electric circuit with the microbial fuel cell compartment;
- an electric switch forming an intermittent connection between the anode, the cathode and the electric impedance load;
- an electric sensor to measure an electric parameter of the electric circuit; and
- a control system coupled to the electric switch and the electric sensor, the control system receiving a measurement from the electric sensor, and outputting an indication signaling the presence or absence of the water contaminant(s) based on the measurement.

In one embodiment a water delivery control is used to provide a controlled water amount to the microbial fuel cell compartment being from 2 to 5% per water delivery event of a total volume of the microbial fuel cell compartment volume.

In one embodiment the biodegradable carbon source is supplied to the anode at a flow rate that is substantially constant.

In one embodiment the biodegradable carbon source is provided in a concentration of between 10 mg/L to 100 mg/L in the anode.

In one embodiment the biosensor further comprises a pumping system to supply the biodegradable carbon source from the storage compartment to the anode.

In one embodiment the autonomous pumping system is a capillary pump system or a timer-controlled programmable pump.

In one embodiment the biodegradable carbon source is a highly concentrated organic material.

In one embodiment the biodegradable carbon source is a solid mass or a gel mass that decays over time by hydrolysis.

In one embodiment the concentration of the biodegradable carbon source at the anode is maintained sufficiently low such that the chemical oxygen demand concentration is between about 10 to about 50 mg/L.

In one embodiment the water contaminants comprise inorganic toxicants.

In one embodiment the inorganic toxicants include at least one of Pb, Hg, Cu, Zn, Cd, Cr, Ag, Ni, Fe, Cl, ammonium or a pesticide.

In one embodiment the water contaminants comprise organic contaminant(s).

In one embodiment the organic contaminants include at least one of a hydrocarbon, a biodegradable organic compound, a hydrocarbon derivative, a bacterial toxin, a phenol compound, a formaldehyde, a diazinon, a sulfamethoxazole, a sulfadiazine, a chloramine, or a polychlorinated biphenyl.

In one embodiment a separator membrane that is ion permeable separates the cathode and the anode.

In one embodiment the membrane is selected from the group consisting of a piece of cloth, a piece of fabric, a proton exchange membrane, an ion exchange membrane, a porous and non-conductive material, and a non-conductive mesh.

In one embodiment the electric sensor measures the electric parameter when the electric switch is ON at intervals of at least 5 minutes to lower an average current of the microbial fuel cell.

In one embodiment the electric sensor measures the electric parameter for a measuring period of no more than 2 minutes.

In one embodiment the anode comprises an electrically conductive material with a large surface area.

In one embodiment the conductive material comprises a material selected from the group consisting of carbon felt, carbon paper and granular carbon.

In one embodiment the cathode is exposed to an oxygen-rich environment.

In one embodiment the biosensor further comprises a floater component.

In one embodiment the cathode contains or is covered with a catalyst.

In one embodiment the catalyst is selected from the group consisting of a manganese oxide of the form $Mn_xO_y$, MnOOH, a noble metal, a combination of carbon with a metallic compound, hybridizing $MnO_2$ with $Ag_4Bi_2O_5$, a transition metal oxide, a manganese-iron mixed oxide doped with $TiO_2$, a layered manganese-cobalt-nickel mixed oxide, a layered copper-manganese oxide, a well-dispersed spinel cobalt-manganese oxide, a cubic $Mn_2O_3$-carbon, a bond competition control manganese oxide and combinations thereof.

In one embodiment the biosensor further comprises an additional sensor selected from the group consisting of a water resistivity sensor, a temperature sensor, a pH sensor, a dissolved oxygen content and a water flow meter.

In a second aspect there is provided a method of monitoring contamination of a body of water with the biosensor according to the first aspect, the method comprising:

obtaining an indication from the biosensor; and determining the presence of a contaminant based on the indication.

Many additional features and combinations thereof concerning the present improvements will appear to those skilled in the art following a reading of the instant disclosure.

DETAILED DESCRIPTION

Figure 1A:
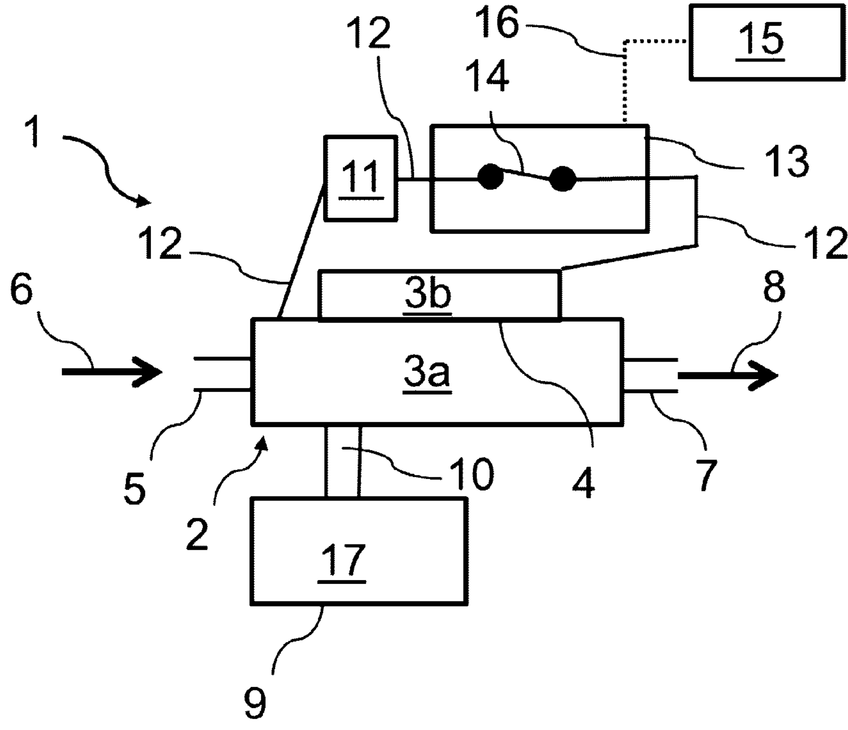
FIG. 1A is a schematic representation of a biosensor microbial fuel cell according to an embodiment of the present disclosure.
Figure 1B:
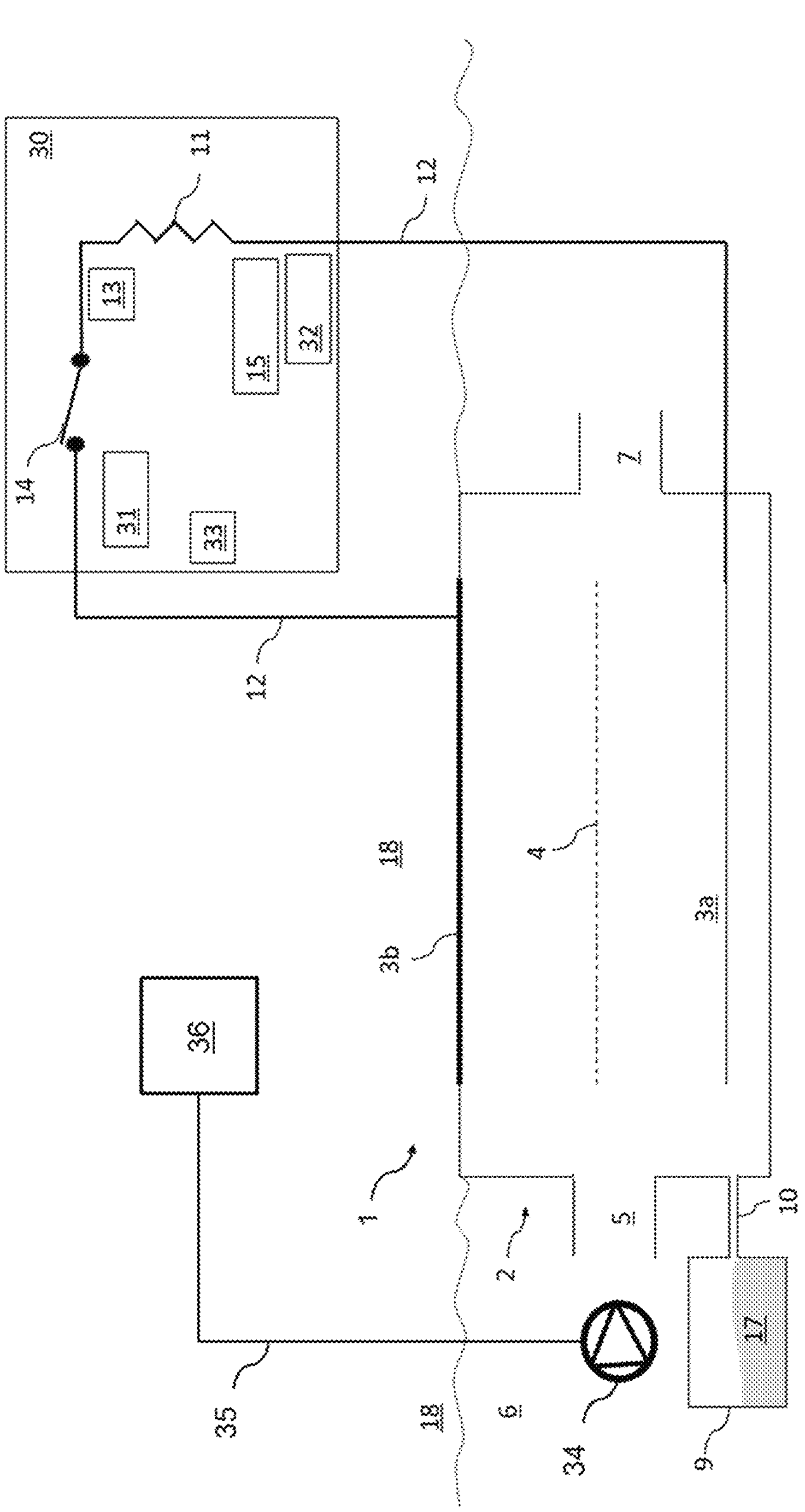
FIG. 1B is a schematic representation of a biosensor microbial fuel cell according to an embodiment of the present disclosure.

Making reference to FIGS. 1A and 1B, there is provided a biosensor 1 for measuring the presence of contaminants in water. In FIG. 1A, the biosensor is surrounded by air. This configuration is referred to as the "flow-through" configuration. In FIG. 1B, the biosensor floats on the surface of a body of water. This configuration is referred to as the "floating" configuration. The biosensor has a microbial fuel cell compartment 2 which comprises an anode 3*a* and a cathode 3*b*. The anode 3*a* is separated electrically and physically from the cathode 3*b* by a fluid-filled gap that allows ion exchange between anode 3*a* and cathode 3*b*. Within this gap, there can also be an optional separator 4 to help separate the anode and the cathode. If the separator 4 is used, it must allow ion exchange between the anode 3*a* and the cathode 3*b*. The separator 4 can be, for example, a membrane such as a proton exchange membrane, a piece of cloth, a piece of fabric, a porous and non-conductive material, or a non-conductive mesh. The microbial fuel cell compartment 2 has inlet 5 to receive water 6 from the body of water that is being monitored. The inlet 5 can be one or more openings in the microbial fuel cell compartment 2, a tube opening, or a tube-like opening. The water 6 flows into the microbial fuel cell compartment 2, encountering the anode 3*a* and the cathode 3*b*. The cathode 3*b* is exposed to an oxygen-rich environment. In one embodiment, the oxygen-rich environment is air or a film of water enriched in oxygen (for example, water exposed to air is subsequently splashed onto the cathode or water near the surface that exchanges oxygen with the air thus maintaining an oxygen rich status). The microbial fuel cell has an outlet 7 at the microbial fuel cell compartment 2 to allow the tested water 8 to exit the microbial fuel cell compartment 2. The outlet 7 can be one or more openings in the microbial fuel cell compartment 2, a tube opening, or a tube-like opening. It is also possible that the inlet 5 and the outlet 7 be the same single or multiple openings in which case water circulation would occur by diffusion, convection, or be caused by water currents external to the microbial fuel cell assembly.

The anode 3*a* is covered, at least in part, and in some embodiments on most of its surface, by a population of electroactive anaerobic microorganisms. It may also be covered in part by aerobic microorganisms. Under normal conditions the population of electroactive anaerobic microorganisms transfers electrons to the anode and generates an electrical current. The current goes through an electric circuit that includes the cathode 3*b*, an electric switch 14, the electric impedance load 11, and reaches the anode 3*a*. Without wishing to be bound by theory, if the switch is in the open circuit condition, this is equivalent to an infinite impedance load and the actual device used as an impedance load 11 is not necessary. The electric sensor 13 comprises the required electronics to sense an electric parameter of the current that depends on the state of the switch (ON or OFF) and on time. In one embodiment, the electric impedance load 11 is a resistor, the switch is ON, and the electric sensor senses the time-varying voltage across the resistor. In the same or in another embodiment, the switch is OFF and the sensor senses the time-varying open circuit voltage between the electrodes 3*a* and 3*b*.

In one example, the electroactive anaerobic microorganisms perform extracellular electron transfer (EET), specifically releasing electrons into the biosensor's electric circuit.

The electroactive microorganisms can alternatively or in addition, have an electron storage capacity. The electroactive microorganisms can also alternatively or in addition be defined as able to lead a Faradaic current flow at the anode. The population of electroactive microorganisms can comprise electroactive bacteria, for example, from the genera *Geobacter* sp. *Shewanellaceae* sp, *Aeromonas* sp, *Pseudomonas* sp, and/or *Desulfuromonas* sp. In one embodiment, the anode comprises electroactive bacteria from the species *Geobacter sulfurreducens*. In order to improve the electrical connections of the electroactive microorganisms and the electric circuit, the anode 3*a* can advantageously be made of a conductive material with a large surface area such as carbon felt. In one embodiment the carbon felt is mechanically secured to a thin stainless steel mesh, incorporated on one side of the anode compartment. The conductive material with a large surface area can also be carbon paper, granular carbon or similar electrically-conductive and porous media.

The anode is maintained in anaerobic or micro-aerobic conditions when the biosensor is in use, to sustain the population of anaerobic electroactive microorganisms and to sustain their function for a long time. Anaerobic conditions, as used herein, can be defined as being completely anaerobic, mostly anaerobic or micro-aerobic.

The anaerobic or micro-aerobic conditions at the anode can be maintained in various ways. It can be maintained by minimizing contact with oxygen-rich environments (unlike the cathode) by insuring that the water that flows through the inlet does not have significant amounts of oxygen. For example, a water body may be highly enriched in oxygen at the surface but the oxygen concentration will typically decrease with depth. Therefore, in one embodiment, the water intake that provides water to the water inlet 5 is maintained below the surface of the water body at a depth with a sufficiently low oxygen concentration to maintain the anode in anaerobic or micro-aerobic conditions. In some embodiments, the depth is at least 20 centimeters, at least 25 centimeters, at least 30 centimeters or at least 50 centimeters. However, the appropriate depth may vary depending on the oxygen concentration gradient in the water body below the water-air boundary. Another method to sustain anaerobic conditions at the anode is to provide the biosensor with means to regulate the amount of water that reaches the anode compartment so that the flow rate is large enough for contaminant detection but small enough for the aerobic microorganisms to completely consume the oxygen and maintain anaerobic conditions. In one embodiment, a water delivery control can be used to provide a controlled water amount to the microbial fuel cell. The water delivery control can be a passive water delivery control or an active water delivery control. The water delivery control provides a controlled water amount in a single or a succession of occurrences referred to as "water delivery event(s)". The expression "passive water delivery control" means that the controlled water amount is controlled by natural external forces such as diffusion, water currents, or waves. The expression "active water delivery control" means that the controlled water amount is controlled by a device that vary and adapt the controlled water amount. In one example, the active water delivery control is a pump system to transport a controlled amount of water into the anode (not shown on FIG. 1A). The pump may be operated intermittently at a higher flow rate, or continuously at a lower flow rate. If an intermittent operation is used one may have to wait for the anode to return to an anaerobic state before a measurement is made. Therefore, if the pump is operated intermittently, it is preferable that the biosensor makes a measurement immediately before the pump is operated rather than immediately after because this favors anaerobic conditions at the anode. In another example, the sizes and distribution of the openings comprised in inlet 5 and outlet 7 are designed to achieve the same result (i.e., flow large enough for detection and small enough for oxygen control) with passive flow or diffusion. In yet another example, the size and distribution of the inlet 5 and outlet 7 is adjustable. In yet another example, there may exist a pressure differential between the inlet and the outlet and an adjustable valve can be used to regulate flow rate. Generally, the inlet 5, outlet 7, and anode compartment are designed so that the waterflow covers most if not all of the anode. It is preferable that there be no area with zero or near zero flow because that portion of the anode over which there is zero flow would not sense changes in water contaminants.

The controlled supply of biodegradable carbon source contributes to the maintenance of anaerobic conditions at the anode and of the stability of the microbial metabolic activity. Making reference to FIGS. 1, 2, and 3, the biosensor 1 has a storage compartment 9 comprising a biodegradable carbon source 17 that serves as a source of nutrients for the electroactive microorganisms. Indeed, it is intended that the electroactive microorganisms consume the biodegradable carbon source 17 for their metabolism, including their respiratory function, and release electrons into the electric circuit. If some oxygen is dissolved in the water 6, the activity of the aerobic microorganisms decreases oxygen concentration and returns the anode to anaerobic conditions. The biodegradable carbon source 17 can be in a solid, gel, or liquid state. In one embodiment, the biodegradable carbon source 17 is highly concentrated. Highly concentrated can be defined as having the carbon source at more than 0.5%, 0.6%, 0.7%, 0.8%, 0.9%, 1% of the total weight in a solvent which is typically water (e.g., 50 g/L (5%) acetate solution). In one embodiment, the biodegradable carbon source 17 comprises one or more of consumable carbohydrates (such as glucose, sucrose, etc.) and acetate. In another embodiment the biodegradable carbon source comprises a mix of sawdust and humus. Other biodegradable carbon source examples include organic materials like peat moss, polylactate, etc.

The biodegradable (nutritional) carbon source 17 can be provided by an opening from the storage compartment 9 to the microbial fuel cell compartment 2. Specifically, the biodegradable carbon source 17 must reach the electroactive microorganisms by either providing the biodegradable carbon source 17 directly to the electroactive microorganisms or indirectly (such as in the vicinity of the electroactive microorganisms). Alternatively, in one embodiment, the supply of biodegradable carbon source 17 is controlled by a pumping system such as a capillary pump system or a peristaltic pump (not shown on FIG. 1A or FIG. 1B) that extends from storage compartment 9 to microbial fuel cell compartment 2, through the communication 10. For the capillary pump system, the communication 10 can be a tube made of a fiber such as silk, cotton, or any suitable material known in the art. To allow proper capillary flow, the biodegradable carbon source 17 must have appropriate viscosity to allow for capillary transport. The capillary pump supplies the biodegradable carbon from source 17 at a substantially constant rate by design of the pump. In the context of the present disclosure, the expression "substantially constant" can be defined as ±10%, ±5%, or ±3%. Depending on the carbon source concentration the pump supplies carbon at a rate that is sufficient to maintain the concentration of organic matter in the range of 10 to 100 mg/L in the vicinity of the anode, such as from 20 to 80 mg/L or about 50 mg/L. In one example, the capillary pump can supply the biodegradable carbon source 17 at a flow rate of between about 0.5 to about 5 mL per day, between about 1 to about 5 mL per day, between about 2 to about 5 mL per day, between about 0.5 to about 20 mL per day or between about 1 to about 20 mL per day. However the flow rate will depend on the concentration of the carbon source and the type of carbon source. In some embodiments, the term "substantially constant supply" means that the carbon source supply rate does not change erratically or by more than, for example, 10% between two successive measurements. For example, an exponentially decaying supply would provide a substantially constant supply of biodegradable material when the decay half-life is much longer than the time between successive measurements.

Figure 1C:
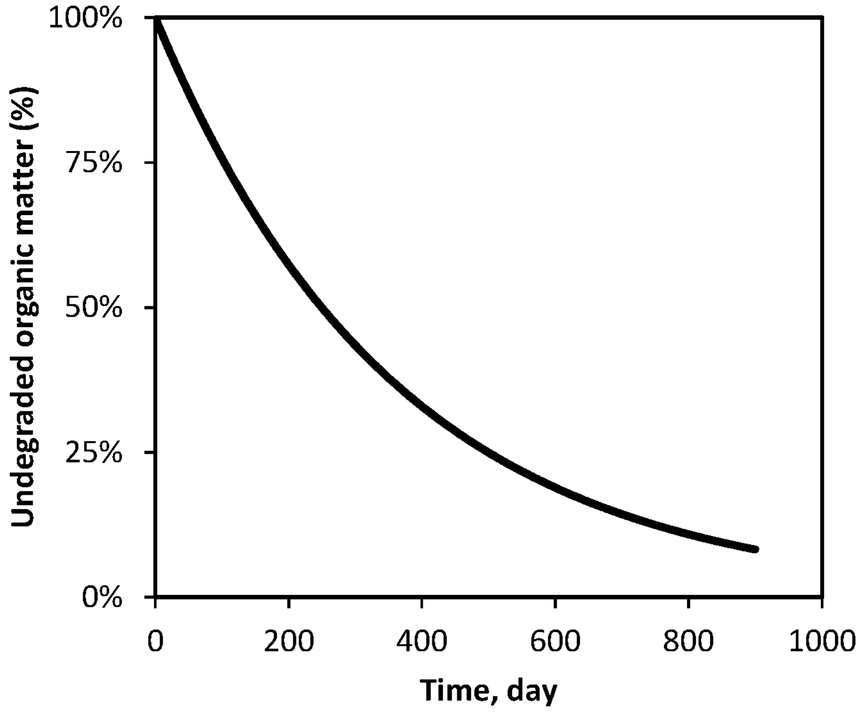
FIG. 1C is a graph showing an exponential decay of the biodegradable carbon source over time.

In a further embodiment, the supply of biodegradable carbon from source 17 is achieved using a mass of biodegradable carbon that decays overtime by hydrolysis, thereby releasing a portion of its mass to supply the anode 3*a*. The mass can be a solid mass or a gel mass. The mass decays at a half-life that is larger than or approximately equal to the period of time during which the biosensor is planned to operate without maintenance. In one embodiment, the mass decays at a half-life of at least about once, at least 1.5 times, at least about 2 times, at least about 2.5 times, or at least about 3 times the time during which biosensor 1 is planned to operate without maintenance. For example, the half-life should be larger than approximately one month if the sensor is to be operated without maintenance for 2 months or more. In another example, the half-life is between about 3 months to about 3 years, between about 3 months to about a year, between about 6 months to about 3 years, between about 6 months and about 1 year. In another example, the half-life is at least about 3 months, at least about 4 months, at least about 5 months, at least about 6 months, at least about 7 months, at least about 8 months, at least about 9 months, at least about 10 months, at least about 11 months or at least about a year. Without wishing to be bound by theory, the decay of the mass is expected to follow an exponential decay model. FIG. 1C shows an exemplary exponential decay graph for a concentrated solid carbon source over time.

In some embodiments, it is advantageous to provide a substantially constant supply of biodegradable (nutritional) carbon source to ensure optimal operation of the biosensor. This substantially constant supply can be achieved using a decaying mass, a capillary pump system, a programmable pump or other means of supplying a substantially constant amount of biodegradable carbon source. The biodegradable carbon source can be supplied at a rate that results in a chemical oxygen demand (COD) concentration of between about 10 mg/L to about 50 mg/L in the anode. The controlled and substantially constant supply of biodegradable carbon is intended to sustain the aerobic and anaerobic microorganism population in the biosensor, especially in the presence of contaminants such as toxicants, and to maintain the anode under anaerobic conditions. In one embodiment, the biodegradable carbon is supplied to the microbial fuel cell compartment 2 at a rate that results in a chemical oxygen demand of between about 10 to about 40 mg/L, between about 10 to about 30 mg/L, between about 20 to about 50 mg/L, or between about 30 to about 50 mg/L.

The anaerobic conditions and the control over the COD in turn, ensure the biosensor is sensitive enough to detect contaminants whose concentration in the water is less than about 100 ppm (part per million), less than 10 ppm, or less than 1 ppm. For example, in some embodiments, contaminants such as methyls and formaldehyde can be detected at concentrations of less than about 100 ppm. In a further example, in some embodiments, cyanotoxins can be detected in concentrations at the ppb (part per billion) range. In yet a further example, in some embodiments, inorganic metal toxicants can be detected at concentrations of less than 100 ppm or even in the ppb range (such as 35 ppb). The biosensor can detect many water contaminants including organic and inorganic toxicants. In one embodiment, inorganic toxicants can be but are not limited to metal ions, ammonium, pesticides, and chlorides. For example, one or more inorganic toxicant(s) can be ammonia, Pb, Hg, Cu, Zn, Cd, Cr, Ag, Ni, and Fe. The organic contaminant(s) include but are not limited to hydrocarbons and derivatives thereof, bacterial toxins (such as, for example, cyanobacteria toxins), phenol compounds, biodegradable organic compounds (such as proteins and carbohydrates) and formaldehyde. For example, the organic toxicant can be diazinon, sulfamethoxazole, sulfadiazine, chloramine, or polychlorinated biphenyl. Some organic contaminants may not be toxic such as proteins, sugars, and other biodegradable compounds.

The microbial fuel cell presented in this disclosure operates at a low current/voltage generation with a limited supply of biodegradable carbon source, intended to reduce the availability of biodegradable carbon source and increase the sensitivity of the biosensor because starved microbes are more sensitive to toxicants. The microbial fuel cell of the biosensor is therefore unlike most other microbial fuel cells that are typically used as batteries and as such are intended to maximise microbial activity to produce as much power as possible. Instead, the microbial fuel cell is operated such that the carbon source provides enough nutrition to keep the microorganisms alive but somewhat starved. Indeed, it is not only useful but also desirable to do measurements when the carbon source is limited (and stable) because it increases the biosensor's sensitivity to contaminants such as toxicants and helps to avoid voltage reversal. Furthermore, without wishing to be bound by theory, if the electrodes are connected continuously to an electric load (resistor) under conditions in which the carbon source is limited, the accuracy and performance of a biosensor will decrease overtime.

Figure 2:
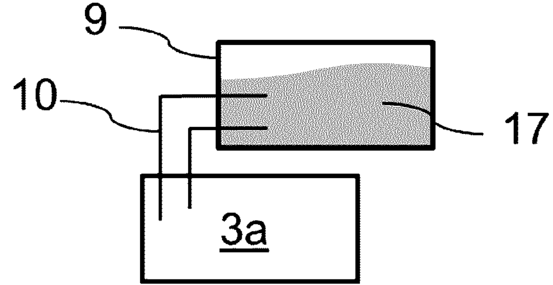
FIG. 2 is a schematic representation of an embodiment of the present disclosure for the carbon supply to the anode using a capillary system.

As can be seen in FIG. 2, in one embodiment, the storage compartment 9 is positioned above the anode 3*a*. This configuration is particularly suitable for a biosensor designed to float in a body of water that is stationary to a certain degree, using floating means such as a mechanical floater. In such an embodiment, water can be delivered to the anode 3*a* by wave action and diffusion. In another embodiment of such type, water can also be delivered to the anode 3*a* by means of a submersible pump 34 controlled by a timer 36 through wires 35 (FIG. 1B). The storage compartment above the anode configuration is also advantageous when a capillary pump system is used to supply the biodegradable carbon source 17. In the floating configuration of FIG. 1B, the anode 3*a* is completely submerged under the water surface while the exterior of the cathode 3*b* is exposed to air 18. Optionally, the biosensor 1 includes a biodegradable carbon source storage compartment 9 that is located underneath the anode 3*a*. Alternatively, the biodegradable carbon source can be delivered by a low power intermittently operated peristaltic pump.

Figure 3:
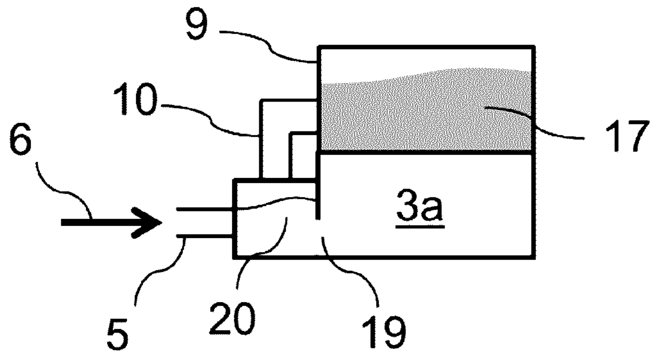
FIG. 3 is a schematic representation of an embodiment of the present disclosure for the carbon supply to the anode using the influent water stream.

In one embodiment, illustrated in FIG. 3, storage compartment 9 has an extension 20 situated adjacent and before the anode in the direction of flow. The extension 20 and the anode are in communication through a channel or opening 19. In a flow-through configuration, the storage compartment 9 or the extension 20 is positioned upstream of the microbial fuel cell compartment 2. The flow-through configuration is particularly suitable for an industrial setting such as in-line water quality monitoring in plants. The water entering the biosensor is supplied some biodegradable carbon by the biodegradable carbon source 17 or a portion thereof in the extension 20 and carries some of the decaying biodegradable carbon to supply the microorganism in anode 3*a* through the opening 19. Having the extension 20 may be advantageous in some embodiments because it can allow the biodegradable carbon to better mix with the inlet water. Other methods of mixing the carbon source with the inlet water are included by reference to the general literature on fluid mechanics.

Returning to FIGS. 1A and 1B, the anaerobic anode 3*a* provides electrons to the aerobic cathode 3*b* where an oxygen reduction reaction (ORR) takes place when the switch 14 is ON, i.e. when the electrical circuit is closed. The cathode 3*b* is designed such that the ORR is not a limiting factor at the microbial fuel cell compartment 2. This is achieved by having a large or substantially unlimited supply of oxygen to the cathode. Oxygen is an advantageous electron acceptor molecule for the microbial fuel cell compartment 2 due to its high redox potential, availability, and sustainability. In one embodiment, the cathode 3*b* is exposed to air, thereby advantageously having access to a substantially unlimited supply of oxygen. In another embodiment, the cathode 3*b* is exposed to a thin film of water which is itself rich in oxygen. For example, this could be water splashes, or the surface layer of a body of water such as a lake. To perform the ORR, the cathode 3*b* has an ORR catalyst. In some embodiments, the cathode is covered with a catalyst such as the ORR catalyst. In one embodiment the ORR catalyst is a manganese oxide. In another embodiment the ORR catalyst is a noble metal or a combination of carbon with a metallic compound. For example, the ORR catalyst can be selected Pt+C, $Mn_XO_Y$ (such as $MnO_2$, $Mn_2O_3$, $Mn_3O_4$, $Mn_5O_8$, and MnOOH) and/or a catalyst made by hybridizing $MnO_2$ with $Ag_4Bi_2O_5$, Other examples include, but are not limited to, transition metal oxides, manganese-iron mixed oxide doped with $TiO_2$, layered manganese-cobalt-nickel mixed oxides, layered copper-manganese oxide, well-dispersed spinel cobalt-manganese oxides, cubic $Mn_2O_3$-carbon, or bond competition control manganese oxide. Catalyst poisoning may occur more often when a Pt catalyst is employed compared to a $MnO_2$ catalyst thus in some embodiments a $MnO_2$ catalyst is selected. Optionally, electron acceptor electroactive microorganisms can be present at the cathode 3*b* to complement the ORR catalyst activity. In some embodiments, the optional separator 4 is permeable to microorganisms; thus the cathode 3*b* can contain microorganisms that originate from the anode 3*a* or from the water body that enters the microbial fuel compartment 2.

As shown in FIG. 1A, the biosensor 1 has an electric impedance load 11 connected to the anode 3*a* and cathode 3*b* with electrical connections 12, such as electrical wires. The electric impedance load connection to the anode and the cathode creates an electrical circuit with the microbial fuel cell. The electric impedance load may be a resistor, a capacitor, an inductor, or a combination thereof, or a passive or active electrical device that impedes the current. In one embodiment, the electric impedance load 11 is a resistor. In another embodiment, the electric impedance load 11 may be variable or electronically adjustable.

As further shown in FIG. 1A, the biosensor 1 also has an electric sensor 13 adapted to measure an electric parameter of the electrical circuit. The electric parameter can be selected from one or more of the current (DC), voltage, or their time dependence. The electric circuit has an electric switch 14 forming an intermittent connection to the microbial fuel cell's electrodes. The electric switch 14 allows to open and close the electric circuit. This allows the operation of the biosensor 1 at lower average current compared to other biosensors based on microbial fuel cells. Moreover, the electric switch 14 is advantageous to measure some electric properties of the electric circuit. For example, the switch 14 can be used to monitor the time dependence of the electric current and voltage after closing or opening. These values can be used for contaminant concentration calculations. Replacing the switch by a variable resistor or any other device that can be set to very low and very high resistance (e.g., between 1 Ohm and 10 MegaOhm) is not substantially different from using a switch and such embodiments are contemplated by the present disclosure.

The switch may be turned ON and OFF repeatedly with a real or complex impedance (i.e. a load with a combination of inductance, capacitance, resistance and active components) and repetitive, AC, measurements can be made. The AC frequency could be fixed or adjustable and so obtain a response at one or many frequencies. All such circuit design variations require an electrical sensor (such as a voltage meter or a current meter) and some type of impedance load and, therefore, are included in this invention by reference to the general electronics literature. Different types of measurements can be used to selectively measure a particular property of the microbial fuel cell.

The biosensor presented in this disclosure contains its own source of biodegradable carbon source and is therefore independent of external carbon source, such as in the tested body of water. This makes it suitable for contaminant monitoring in bodies of water with low and/or unstable carbon supply. It also makes the sensor insensitive to signal interference due to COD concentration changes in the surface water. Such COD fluctuations would in turn lead to a false positive contamination measurement, a weakness often found in most prior art biosensors.

The carbon-source deprived microorganisms will be stressed and will decay over time if the electrical circuit is always closed (with the switch 14 always ON). The biosensor presented in this disclosure can overcome this limitation by performing intermittent measurements using the electric switch 14 that creates an intermittent connection. For example, the electric parameter is measured for equal to or less than 2 minutes, equal to or less than 1.5 minutes, equal to or less than 1 minute, or equal to or less than 30 seconds. In some embodiments, the interval between measurements is of at least 5 minutes, at least 6 minutes, at least 7 minutes, at least 8 minutes, at least 9 minutes, at least 10 minutes, at least 20 minutes. In further embodiments, the interval between measurements is from 30 seconds to 12 hours, from 1 minute to 12 hours, from 1.5 minutes to 12 hours or from 2 minutes to 12 hours. In yet further embodiments, the electric parameter is measured for 30 seconds every 10 minutes, for 1 minute every 20 minutes, or for 2 minutes every 12 hours. Thus in one embodiment, the electric sensor measures the electric parameter for a period of time between 30 seconds to 2 minutes at intervals ranging from 10 minutes to 12 hours or more. The combination of using an electric switch and a stable biodegradable carbon source allows to increase and adjust the sensitivity of the biosensor and to make the measurements more stable.

Figure 4:
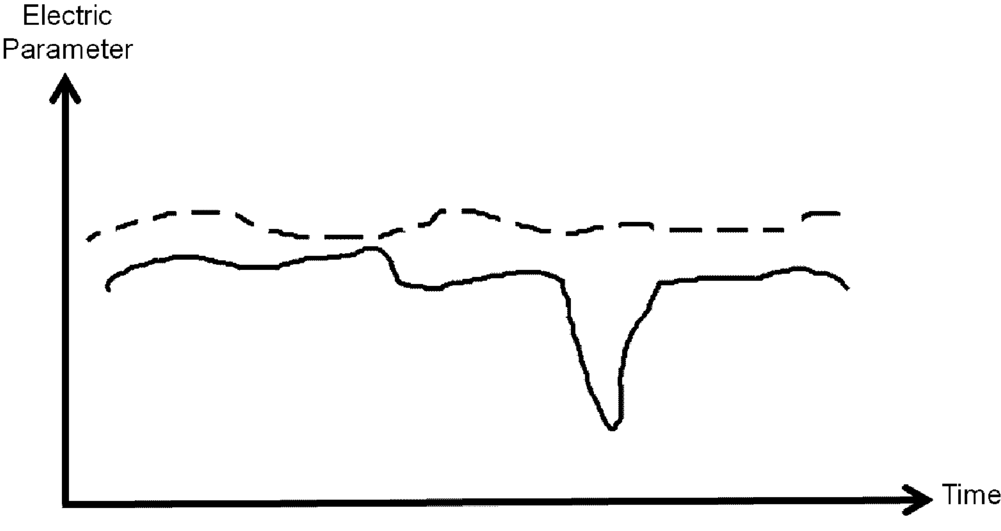
FIG. 4 is a graph illustrating the potential variation of the electric parameter over time when there is no contamination (dotted line) compared to when a contamination event occurs (full line)

As shown in FIG. 1A, the electric sensor 13 also includes a control system 15 and various components, including optionally a power source. The sensing device (such as voltmeter or ammeter) is the actual device that measures the electric properties of the circuit. For example, the sensing device can be a voltmeter or an analog to digital converter. The control system 15 activates and regulates the various capabilities of the sensor and pump(s) in some embodiments. In particular, it controls the activation of one or more electric switch(es) 14, adjusts the value of the electric impedance 11 (if it is adjustable) and determines if the electric parameter sensed by the sensing device corresponds to the presence of a water contaminant. The control system controls also the activation and deactivation of pumps used for water circulation or carbon source delivery in some embodiments. The control system may use a clock to determine when to open and close the electric switch(es) and when to collect the electrical parameters sensed by the sensing device. Finally, the control system 15 optionally operates a communication device to communicate a signal and/or any other information useful in the use and maintenance of the biosensor. The communication device can be a visual or audible indicator, a display screen, a removable memory, an electronic communication device such as a USB or Ethernet connexion, or a wireless communication device. In one example, minimally, the control system could be a human being, the electric switch could be a mechanical device that is manually activated, the clock could be the sun, the communication device could be the human voice. However, it is advantageous to automate these functionalities and that the electric sensor be an automated electronic system. The electric sensor also requires a power source that can be internal (such as batteries) or external (such as a power supply) to the electric sensor 13 with a physical or wireless connection 16 (FIG. 1A). FIG. 1B shows an internal power supply 31. The electric sensor must be linked to the microbial fuel cell with electric wires 12. The electric sensor 13, pump(s) and the microbial fuel cell compartment 2 may be assembled into one physical unit, or the wires 12 may be made longer so that the electric sensor, pump(s) and the microbial fuel cell are different units linked by the wires 12 as shown in FIG. 1B. Thus, the electric sensor 13 can be part of the biosensor 1 installation at the water body. FIG. 1B illustrates the embodiment where the anode 3*a* is submerged in water 6 and the cathode 3*b* is exposed to air 18. The biosensor 1 can include within the same physical unit 30, the control system 15, pump 34, a power source 31, a clock 32, an electric sensor 13, and a communication device 33. In one embodiment, the control system 15 is an analog electronic circuit. However, nowadays, an embodiment of the control systems 15 that is often more practical may be digital microprocessors such as a field programmable gated array (FPGA), or a digital microprocessor or microcontroller, with an operating system that can support an in situ data processing algorithm to interpret the measurement and communicate the presence of contamination. For example, the algorithm may interpret a change in an electric parameter such as a modulation in a curve of the electric parameter overtime. The modulation is caused by a decrease or an increase in the current below/above a certain sensitivity threshold when a contaminant is present. Contaminants that are electron donors (such as biodegradable organic compounds, ammonium compounds and the like) increase the current while electron acceptors (such as toxic metal ions) or toxic species (e.g. hydrocarbons) cause a decrease in the current. The algorithm can also compare the value of the electric parameter, or any combination of electric parameters, to a predetermined threshold to establish whether the detected event is a contamination or not. FIG. 4 illustrates a graph of the sensor voltage over time. The dashed line represents a scenario with no contamination and the solid line represents a scenario with a contamination event, in this case a Cu(II) contamination. The contamination event can be observed in the graph as a modulation, such as a trough, in the curve.

Figure 5:
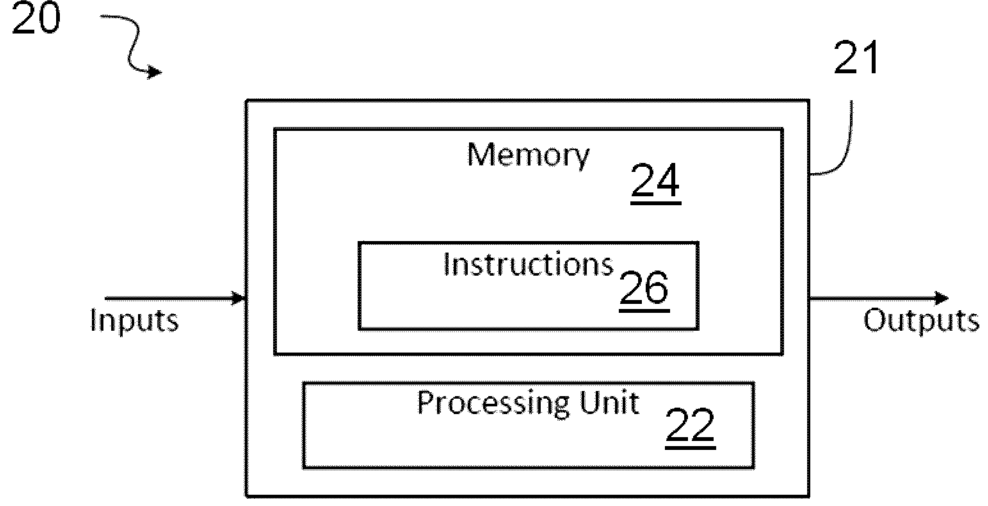
FIG. 5 is a schematic representation of a computing assembly according to an embodiment of the present disclosure.

The biosensor presented in this disclosure also includes a computing assembly as a control system. With reference to FIG. 5, the control system 15 may comprise a computing assembly 20 comprising a computing device 21. The computing device 21 can have the role of a controller. In one embodiment, the control system 15 has a low power microcontroller with analog to digital converter, optionally a real-time clock with sleep and wake up functionality. The computing device 21 comprises a processing unit 22 and a memory 24 which has stored therein computer-executable instructions 26. The processing unit 22 may comprise any suitable devices configured to implement the functionality of the control system 15 such that instructions 26, when executed by the computing device 21 or other programmable apparatus, may cause the functions/acts/steps performed by the control system 15 as described herein to be executed. The processing unit 22 may comprise, for example, any type of general-purpose microprocessor or microcontroller, a digital signal processing (DSP) processor, a central processing unit (CPU), an integrated circuit, a field programmable gate array (FPGA), a reconfigurable processor, other suitably programmed or programmable logic circuits, custom-designed analog and/or digital circuits, or any combination thereof.

The memory 24 may comprise any suitable known or other machine-readable storage medium. The memory 24 may comprise non-transitory computer readable storage medium, for example, but not limited to, an electronic, magnetic, optical, electromagnetic, infrared, or semiconductor system, apparatus, or device, or any suitable combination of the foregoing. The memory 24 may include a suitable combination of any type of computer memory that is located either internally or externally to device, for example random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. The memory 24 may comprise any storage means (e.g., devices) suitable for retrievably storing machine-readable instructions 26 executable by processing unit 22.

The methods and systems described herein may be implemented in a high level procedural or object-oriented programming or scripting language, or a combination thereof, to communicate with or assist in the operation of a computer system, for example, the computing assembly 20. Alternatively, the methods and systems described herein may be implemented in assembly or machine language. The language may be a compiled or interpreted language. Program code for implementing the methods and systems for monitoring the electrical parameters may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods and systems described herein may also be considered to be implemented by way of a non-transitory computer-readable storage medium having a computer program stored thereon. The computer program may comprise computer-readable instructions which cause a computer, or more specifically, the processing unit 22 of the computing device 21, to operate in a specific and predefined manner to perform the functions described herein.

Computer-executable instructions may be in many forms, including program modules, executed by one or more computers or other devices. Generally, program modules include routines, programs, objects, components, data structures, and the like, that perform particular tasks or implement particular abstract data types. Typically the functionality of the program modules may be combined or distributed as desired in various embodiments.

Optionally, the microbial fuel cell's electrical behaviour may be modeled with one of the suitable equivalent circuit models found in the literature. The control system 15, the impedance load 11, the clock, and the sensing device may be operated in such a way as to measure the components of the equivalent circuit model. A suitable combination of the equivalent circuit model components can then be used to estimate contaminant concentration. This is advantageous because the equivalent circuit model parameters are independent from each other and because they can offer a complete characterization of the microbial fuel cell response. However, without wishing to be bound by theory, because the estimation of the equivalent circuit model components is itself a combination of the electrical parameters measured by the sensing device, this method of estimating toxicity is not substantially different from that which is described elsewhere in this document.

In some embodiments, all components are selected to run on as little electrical energy as possible so that the biosensor may be operated autonomously for extended periods of time on relatively small batteries or on energy harvesting devices such as solar cells. In some embodiments, the biosensor of the present disclosure is adapted for autonomous activity during a long period of time. For example, the biosensor can operate autonomously over at least about 3 months, at least about 4 months, at least about 5 months, at least about 6 months, at least about 7 months, at least about 8 months, at least about 9 months, at least about 10 months, at least about 11 months, at least about a year, at least about a year and a half, or at least about 2 years. "Autonomous" and derivatives thereof such as "autonomously" are defined herein as requiring limited or no human intervention such as for replenishment of perishables (such as the biodegradable carbon source) or device maintenance. This can be achieved by selecting components that consume very little power and providing an onboard power source such as a large enough battery or some energy harvesting device such as solar cells. The biosensor can optionally further comprise one or more of a protective housing, a floater component, a telecommunication device (emitter and receiver), a geolocation device, a further electric sensor, a temperature sensor, a pH sensor, or a flow meter. The biosensor may contain a means to trigger an alarm so that some remedial action may be taken. The biosensor also optionally comprises a battery to power any electronic device or sensor that requires it. The battery may be rechargeable for example through solar or wind power, or some other energy harvesting device such as a device that converts motion caused by water waves into energy. The protective housing can be used to protect against the environment, debris, falling leaves, and waves. The floater component can be used to maintain the biosensor's cathode at or above the water surface while, for example, submerging the anode. When the biosensor is deployed in a remote location, the geolocation device can be used to track the location of the biosensor.

More than one biosensor 1 in the floating configuration can be operated in the same water body to increase the total detection area. Moreover, they can be interconnected to share information and better assess water quality of large water bodies.

In general, the biosensor of the present disclosure is a non-specific sensor, that is its response to toxicity does not permit to identify which toxicant is present and its response to organic contaminants that increase oxygen demand does not permit to identify the chemical that increases oxygen demand. However, when the device is deployed in an area where a specific contamination is known to be the main contaminant, copper ion concentration for example, then the control system 15 may be modified to estimate the concentration of that specific toxicant using some form of calibration.

Although this document describes the application of the biosensor to toxicity measurements, the sensor can also be used as an inverse toxicity sensor. That is the sensor can also sense water conditions that promote microbial fuel cell activity. For example, if there is an increase in nutriments or carbon sources in the water being tested (in addition to that supplied by the carbon source compartment 9), this can be registered by the sensor. Therefore, the sensor can also be used to detect surface water runoff, soil erosion, biological oxygen demand (BOD) and chemical oxygen demand (COD). More generally, the sensor can detect any condition that will increase or decrease microbial fuel cell activity. For example, it could even be used as a temperature sensor. However, in the case of temperature, an embodiment of the biosensor would include a temperature sensor to measure water temperature and the temperature value would be used by the control system 15 to increase the accuracy or reliability of the toxicity measurement using an appropriate algorithm. More generally, the control system 15 can use any other available and relevant information to increase the reliability and accuracy of its estimation of toxicity.

Although this document describes the sensor in various embodiment for use as a floating device, this need not be so. Referring to FIG. 1A, the microbial fuel cell compartment 2 may be made substantially water-tight, the inlet 5 and outlet 7 may be hooked up to pipes or tubing in which water circulates, and the microbial fuel cell and sensing unit could operate in air. In this flow-through configuration, the biosensor could measure the toxicity of any water stream that is diverted or pumped to the sensor. This water stream could be, for example, water being processed in a water treatment plant or some water pumped from some local water body or water supply.

The present disclosure includes in its scope the methods of usage of the biosensor and methods using the biosensor. Accordingly, there is provided a method of monitoring the contamination of a body of water, comprising: obtaining an indication from the biosensor according to the present disclosure and determining the presence of a contaminant based on the indication. In addition, there is provided a method of monitoring the contamination of a body of water, comprising: providing the biosensor according to the present disclosure in the body of water; and performing a contamination test on the body of water near the biosensor if the biosensor signals the presence of a water contaminant through the indication, to confirm and identify the identity of the water contaminant. The methods of the present disclosure may also comprise the step of utilizing an equivalent circuit model of the biosensor, determining the equivalent circuit model component values using the electrical sensor and the electric switch, and utilizing one or several of the electrical model component values in assessing the presence of contaminants. The methods of the present disclosure can also further comprise monitoring or measuring one or more of the water resistivity, the temperature, the pH, the dissolved oxygen content and the flow rate of the water. In addition, the methods of the present disclosure may further comprise triggering a signal when contaminants are detected to enable swift remediation of the contamination. Further, there is provided the use of the biosensor according to the present disclosure to trigger an alarm when the biosensor detects the presence of one or more contaminants in the body of water. As the biosensor of the present disclosure is sensitive but does not determine the type of contamination, there is further provided that the method can include performing an additional contamination test or procedure to identify more precisely the cause of the alarm and/or to determine the best course of action in response to the contamination. Moreover, there is provided the use of the biosensor according to the present disclosure in an environment where one parameter is responsible for most of the sensor indication signaling variation; and the use of a calibration to quantitatively correlate the sensor indication to the varying parameter. And finally, there is provided a method for compensating the biosensor according to the present disclosure against the effect of changes in temperature.

Example 1 Flow-Through Biosensor

In the present example, a flow-through biosensor with an integrated constant carbon source delivery system (approximately 50 mg $L^{-1}$ of COD was maintained at all times) was used to detect the appearance of toxicants in tap water. Spikes of chlorine, formaldehyde, microcystins were introduced in tap water fed to the biosensor. Detection of Cl spike was evaluated because it is used for water treatment, while formaldehyde sometimes occurs naturally. Microcystins (from *Microcystis aeruginosa*) were also evaluated, as these compounds can be introduced into tap water distribution networks during cyanobacterial blooms. Particularly, microcystins are very toxic at concentrations as low as 10 μg $L^{-1}$ and can be difficult to detect. During the toxic spike detection tests carried out, tap water being fed to the biosensor was spiked with the either chlorine, formaldehyde or microcystin. The open circuit voltage (mV) of the biosensor was monitored during the shock tests.

Figure 6:
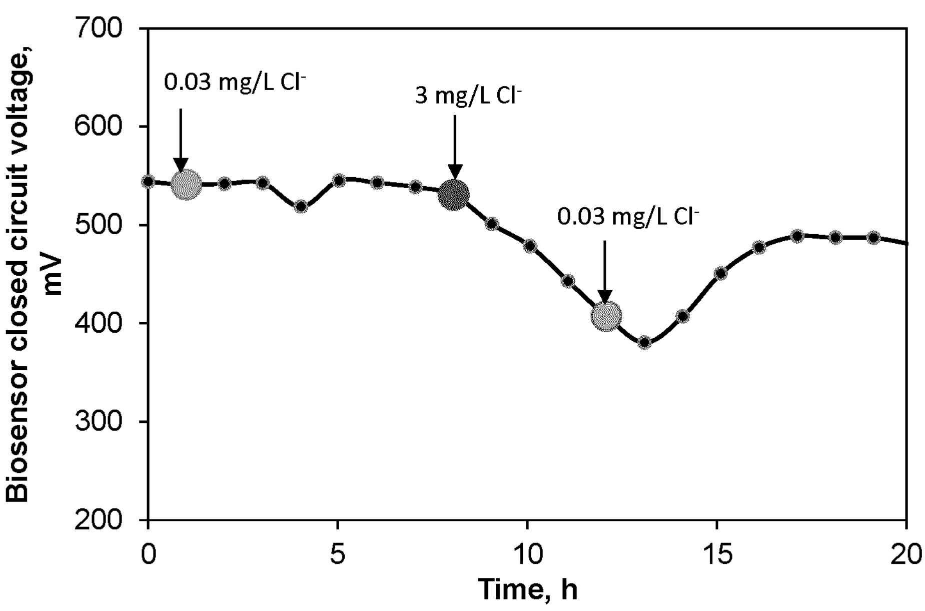
FIG. 6 is a graph showing the detection of a $Cl^-$ contamination event (voltage in function of time)

FIG. 6 shows the voltage measurements for the $Cl^-$ contamination test. Specifically, the non contaminated tap water had a concentration of 0.03 mg/L of $Cl^-$ and the toxicity event introduced was increasing the concentration of $Cl^-$ to 3 mg/L at the time marked by the red dot near 8 hours. As can be seen on the graph, the contamination event leads to a decrease in the voltage until the contamination was cleared at the next green dot near 12 hours. After that, the voltage was restored to a constant plateau. More specifically, after a brief increase (over 4 hours) in the concentration of chlorine to 3 mg $L^{-1}$ (a 100× increase over background level found in tap water), the open circuit voltage of the biosensor decreased. A recovery after the reintroduction of tap water can be seen to lead to an increase in the open circuit voltage.

Figure 7:
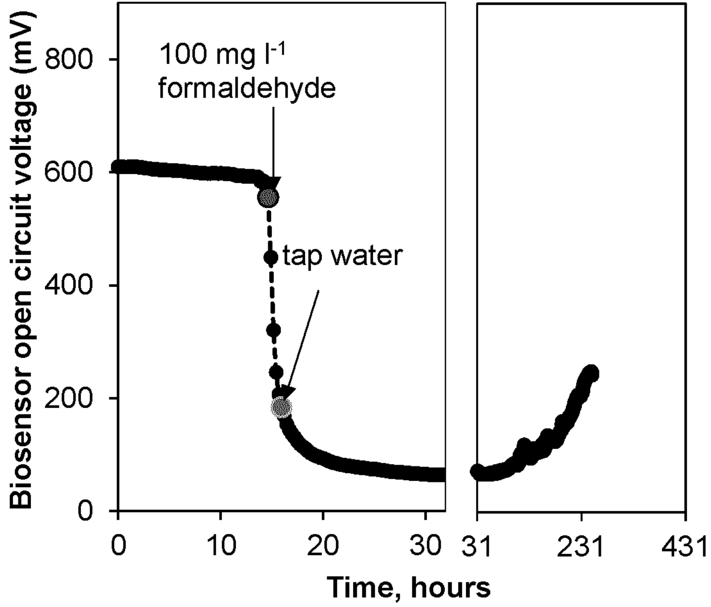
FIG. 7 is a graph showing the detection of a formaldehyde contamination event (voltage in function of time)

FIG. 7 shows the voltage measurements for the formaldehyde contamination test. Specifically, the contamination event was to increase the concentration of formaldehyde to 100 mg/L in tap water at the time marked on the graph. When exposed to 100 mg/L formaldehyde, the biosensor showed a rapid response with an approximate 90% decrease in the estimated open circuit voltage. After being switched back to clean tap water, a slow recovery of the biosensor could be observed. This slow recovery can be attributed to the slow elimination of formaldehyde molecules.

Figure 8:
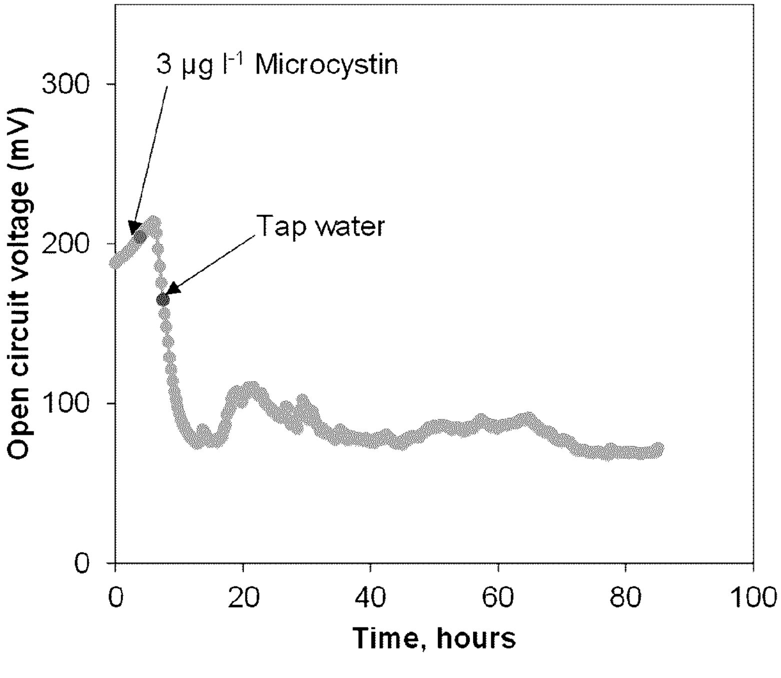
FIG. 8 is a graph showing the detection of a mycrocystin contamination event (voltage in function of time).

FIG. 8 shows the voltage measurements for the microcystin contamination test. Microcystin presence in tap water was quickly detected by the biosensor. The open circuit voltage of the biosensor decreased by 75% when 3 μg/L of microcystin was introduced, demonstrating a relatively high sensitivity of the biosensor to some hard to detect toxicant. The biosensor signal recovered 380 hours after the exposure to the microcystin.

Example 2 Floating Biosensor

Figure 9:
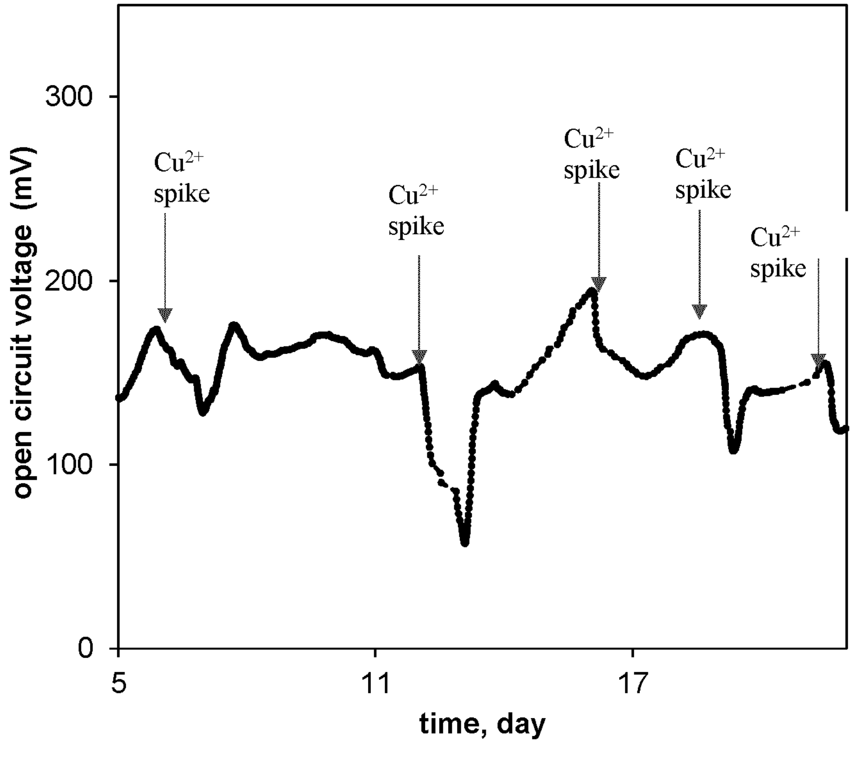
FIG. 9 is a graph showing the detection of copper contamination events (voltage in function of time).

A floating biosensor was suspended in moderately hard water (MHW) composed of (in mg/L): $CaSO_4$ (60), $MgSO_4$ (122.86), $NaHCO_3$ (96), and KCl (4) as an environmental body background reference. Subsequently, Cu contamination was achieved by spiking the MHW reservoir with a $CuSO_4$ stock solution to achieve Cu concentrations of not more than 774 μg/L. To reduce transport related diffusion limitations a sparger was introduced in the tank. FIG. 9 shows the results 5 days after suspension of the floating biosensor in MHW, spikes of Cu were detected by the biosensor. The open circuit voltage reduced with each Cu spike suggesting that the Cu reduces the measurable microbial electroactivity presumably through toxicity to the electroactive microorganisms and the a pathway switch to an electrochemical reduction of $Cu^{2+}$.

Example 3 Onsite Monitoring

Figure 10:
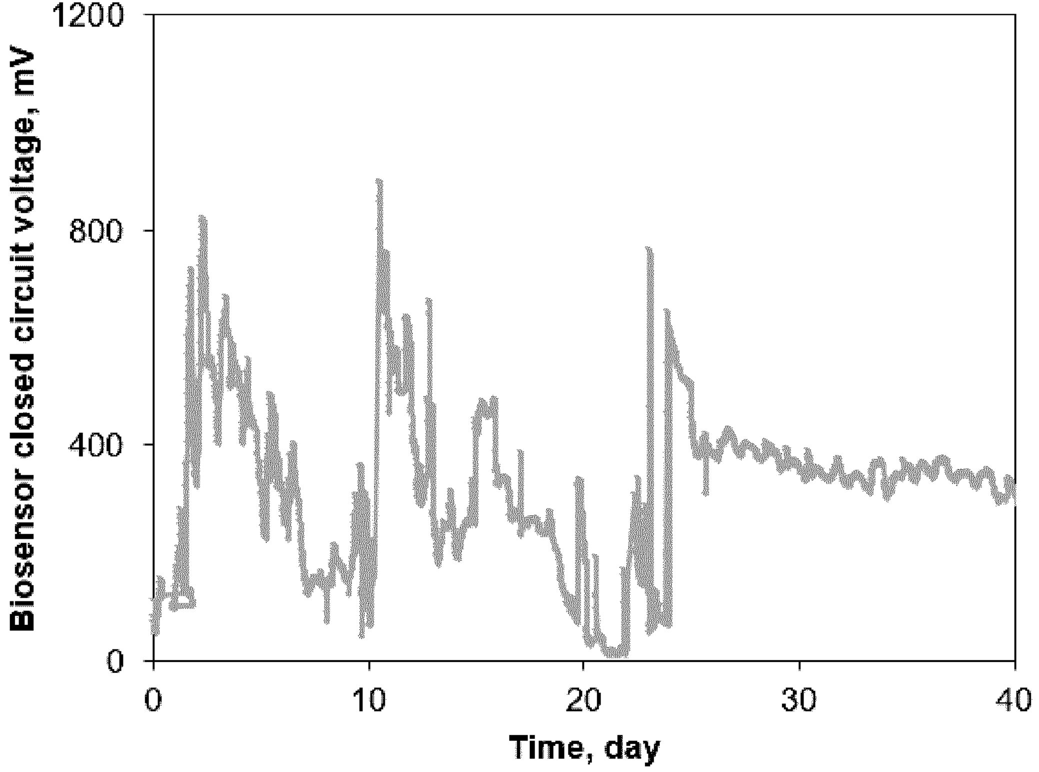
FIG. 10 is a graph showing a continuous monitoring of heavy metal contaminants on the field.

FIG. 10 shows an exemplary graph measurement from onsite monitoring. The closed circuit voltage under constant load can be seen fluctuating much more than in a controlled laboratory environment due to daily variations of temperature and rainfall events causing contaminant concentration changes.

As seen therefore, the examples described above and illustrated are intended to be exemplary only. The scope is indicated by the appended claims.

What is claimed is:

1. A biosensor for detecting water contaminants comprising a microbial fuel cell compartment, the microbial fuel cell compartment comprising (i) at least one opening to allow water into and out of the microbial fuel cell compartment, (ii) an anode comprising electroactive microorganisms, and (iii) a cathode, wherein:

the anode is electrically and physically separated from the cathode, the anode is anaerobic or micro-aerobic and comprises electroactive microorganisms, and the cathode is aerobic;

a storage compartment comprising a biodegradable carbon source, the storage compartment being in communication with the anode to supply the biodegradable carbon source to the electroactive microorganisms at a controlled rate to maintain the chemical oxygen demand (COD) at the anode between about 10 mg/L to about 50 mg/L;

an electric impedance load electrically connected to the anode and the cathode thereby forming an electric circuit with the microbial fuel cell compartment;

an electric switch within the electric circuit forming an intermittent electrical connection between the microbial fuel cell compartment and the electric impedance load;

an electric sensor within the electric circuit to measure an electric parameter of the electric circuit; and a control system coupled to the electric switch and the electric sensor, the control system configured to receive a measurement from the electric sensor, and outputting an indication signaling the presence or absence of the water contaminants based on the measurement, wherein the control system is configured to intermittently activate the electric switch for a period of time, a measuring period, to allow measurement of the electric parameter, such that during operation of the biosensor the electric switch is off between measuring periods.

2. The biosensor according to claim 1, wherein a water delivery control is used to provide a controlled water amount to the microbial fuel cell compartment being from 2 to 5% per water delivery event of a total volume of the microbial fuel cell compartment volume.

3. The biosensor according to claim 1, wherein the biodegradable carbon source is supplied to the anode at a flow rate that is substantially constant.

4. The biosensor according to claim 1, wherein the biodegradable carbon source is provided in a concentration of between 10 mg/L to 100 mg/L in the anode.

5. The biosensor according to claim 1, further comprising a pumping system to supply the biodegradable carbon source from the storage compartment to the anode.

6. The biosensor according to claim 5, wherein the pumping system is a capillary pump system or a timer-controlled programmable pump.

7. The biosensor according to claim 1, wherein the biodegradable carbon source is a highly concentrated organic material, a solid mass or a gel mass that decays over time by hydrolysis.

8. The biosensor according to claim 1, wherein the water contaminants comprise inorganic toxicants or organic contaminants.

9. The biosensor according to claim 8, wherein the inorganic toxicants include at least one of Pb, Hg, Cu, Zn, Cd, Cr, Ag, Ni, Fe, Cl, ammonium or a pesticide.

10. The biosensor according to claim 8, wherein the organic contaminants include at least one of a hydrocarbon, a biodegradable organic compound, a hydrocarbon derivative, a bacterial toxin, a phenol compound, a formaldehyde, a diazinon, a sulfamethoxazole, a sulfadiazine, a chloramine, or a polychlorinated biphenyl.

11. The biosensor according to claim 1, wherein a separator membrane that is ion permeable separates the cathode and the anode.

12. The biosensor according to claim 11, wherein the separator membrane is selected from the group consisting of a piece of cloth, a piece of fabric, a proton exchange membrane, an ion exchange membrane, a porous and non-conductive material, and a non-conductive mesh.

13. The biosensor according to claim 1, wherein the interval between the measuring periods is at least 5 minutes.

14. The biosensor according to claim 13, wherein each of the measuring periods has a duration of equal to or less than 2 minutes.

15. The biosensor according to claim 1, wherein the anode comprises an electrically conductive material with a large surface area.

16. The biosensor according to claim 15, wherein the conductive material comprises a material selected from the group consisting of carbon felt, carbon paper and granular carbon.

17. The biosensor according to claim 1, wherein the cathode is exposed to an oxygen-rich environment.

18. The biosensor according to claim 1 further comprising a floater component.

19. A method of monitoring contamination of a body of water with the biosensor according to claim 1, the method comprising:

obtaining an indication from the biosensor; and determining the presence of a contaminant based on the indication.

* * * * *